United States Patent [19]

Phibbs et al.

[11] 4,195,034

[45] Mar. 25, 1980

[54] PROCESS FOR THE MANUFACTURE OF N-(SUBSTITUTED)-3-AMINOACRYLONITRILES

[75] Inventors: Murray K. Phibbs, Bath; Peter A. Sipos, Kingston, both of Canada

[73] Assignee: Du Pont of Canada Limited, Montreal, Canada

[21] Appl. No.: 963,082

[22] Filed: Nov. 22, 1978

[30] Foreign Application Priority Data

Nov. 25, 1977 [CA] Canada .................................. 291729

[51] Int. Cl.$^2$ .......................................... C07C 120/00
[52] U.S. Cl. .......................... 260/465 E; 260/465.5 R
[58] Field of Search ................... 260/465.5 R, 465 E

[56] References Cited

U.S. PATENT DOCUMENTS 3,001,995  9/1961  Frazza et al. .............. 260/465.5 R X

OTHER PUBLICATIONS

C.A., 76 (1972), Kostyanovskii, et al., 45512d.
C.A., 86 (1977), Hong, et al., 29183y.
Broeckx, et al., Tetrahedron 27(15), 1971, pp. 3527-3534.
Kostyanovskii, et al., C.A., 63, (1965), 1684c, as well as english translation of original paper.
Scotti, et al., 29, (1963), J. Org. Chem., pp. 1800-1808.
Papa, 31, (1965), J. Org. Chem., pp. 1426-1430.

*Primary Examiner*—Joseph Paul Brust
*Attorney, Agent, or Firm*—F. J. Crowley

[57] ABSTRACT

A process for the manufacture of N-(substituted)-3-aminoacrylonitriles of the formula N—($R_1R_2$)—CH=CH—CN where $R_1$ is alkyl, phenyl, phenyl substituted with alkyl and/or —$NH_2$ groups, or —$(CH_2)_n$—NH—CH=CH—CN and $R_2$ is hydrogen or alkyl with the proviso that when $R_1$ is —$(CH_2)_n$—NH—CH=CH—CN $R_2$ is hydrogen, n being 1 to 8. The process comprises contacting cyanoacetylene with the appropriate amine in the presence of an inert atmosphere and at low temperatures, especially less than 40° C., and recovering the product at a temperature of not greater than 50° C.

8 Claims, No Drawings

PROCESS FOR THE MANUFACTURE OF N-(SUBSTITUTED)-3-AMINOACRYLONITRILES

BACKGROUND OF THE INVENTION

1. Field of the Invention

The present invention relates to the manufacture of N-(substituted)-3-aminoacrylonitriles. In particular the invention relates to the manufacture of compounds of the formula $N(R_1R_2)$—CH=CH—CN where $R_1$ is alkyl, phenyl, phenyl substituted with alkyl and/or —$NH_2$ groups, or —$(CH_2)_n$—NH—CH=CH—CN and $R_2$ is hydrogen or alkyl with the proviso that when $R_1$ is —$(CH_2)_n$—NH—CH=CH—CN $R_2$ is hydrogen, n being 1 to 8.

2. Description of the Prior Art

Processes for the manufacture of N-(alkyl)x-3-aminoacrylonitriles, also known as alkyl-beta-cyanovinylamines, are known. For example in U.S. Pat. No. 3,001,995, which issued Sept. 26, 1961, E. J. Frazza et al disclose a process in which beta-chloroacrylonitrile is reacted with an amine, e.g., dimethylamine, in an inert reaction medium preferably in the presence of a hydrogen chloride acceptor. As exemplified by Frazza et al dimethyl-beta-cyanovinylamine was subsequently obtained, when the amine was dimethylamine, in 77% yield by distillation at 93°–99° C. at 0.6–1.0 mm Hg pressure and n-butyl-beta-cyanovinylamine was obtained, when the amine was butylamine, in two fractions giving a total yield of 47% by distillation at temperatures of up to 121° C. It has also been disclosed in Chemical Abstracts 76 45512d (1972) in an abstract of an article by R. G. Kostyanovskii et al that cis-beta-(di-tert-butylamino)acrylonitrile may be obtained from cyanoacetylene in 7 days in 66% yield by a stereospecific reaction at room temperature in the absence of solvent. A process for the manufacture of N-(dimethyl)-3-aminoacrylonitrile from acrylonitrile in less than 50% yield is also known.

N-($R_1R_2$)-3-aminoacrylonitriles have various uses. For example, they may be polymerized with other ethylenically unsaturated monomers to give copolymers containing basic centers. Such copolymers find utility in the field of synthetic fibers when acid dyes are used as well as in ion exchange resins and oil additives.

SUMMARY OF THE INVENTION

An improved process for the manufacture of N-($R_1R_2$)-3-aminoacrylonitriles has now been found.

Accordingly, the present invention provides a process for the manufacture of N-(substituted-3-aminoacrylonitriles of the formula N-($R_1R_2$)—CH=CH—CN where $R_1$ is alkyl, —$(CH_2)_n$—NH—CH=CH—CN, phenyl or phenyl substituted with alkyl and/or —$NH_2$ groups and $R_2$ is hydrogen or alkyl with the proviso that when $R_1$ is —$(CH_2)_n$—NH—CH=CH—CN $R_2$ is hydrogen, n being 1 to 8, said process comprising the steps of:

(a) contacting cyanoacetylene with an amine selected from the group consisting of (i) $NHR_1R_2$, where $R_1$ is alkyl phenyl or phenyl substituted with alkyl and/or —$NH_2$ groups and $R_2$ is as above, and (ii) $NH_2$—$(CH_2)_n$—$NH_2$, where n is 1 to 8, in the presence of an inert atmosphere and at a temperature below the boiling point of cyanoacetylene and of said amine, said temperature being not greater than 40° C., with the proviso that when $R_1$ is alkyl or —$(CH_2)_n$—NH—CH=CH—CN the temperature is not greater than 30° C., and (b) recovering the N-($R_1R_2$)-3-aminoacrylonitrile so obtained at a temperature not greater than 50° C.

In a preferred embodiment of the process of the present invention the cyanoacetylene is contacted with the amine in the presence of an inert solvent.

In another embodiment of the process, the substituent $R_2$ is hydrogen.

In a further embodiment of the process, the substituent $R_1$ is —$(CH_2)_n$—NH—CH=CH—CN with, in particular, n being 6 in which event the amine is hexamethylene diamine.

In the process of the present invention cyanoacetylene is contacted with an amine. The amine may be an amine of the formula $NHR_1R_2$ where $R_1$ is alkyl, phenyl or phenyl substituted with alkyl or —$NH_2$ groups and $R_2$ is hydrogen or alkyl. Alternatively if the desired product is N-($R_1R_2$)-3-aminoacrylonitrile where $R_1$ is —$(CH_2)_n$—NH—CH=CH—CN, where n is 1 to 8, and $R_2$ is hydrogen i.e., an N,N'bis(3-acrylonitrile)alkylene diamine, an alkylene diamine of the formula $NH_2$—$(CH_2)_n$—NH, where n is 1 to 8, is used. In a preferred embodiment n is 6. Preferably $R_2$ is hydrogen. In addition it is preferred that the alkyl groups have 1–6 carbon atoms and that the substituted phenyl groups be substituted in the para position.

DETAILED DESCRIPTION

The cyanoacetylene may be brought into contact with the amine at a controlled rate or the amine may be brought into contact with cyanoacetylene at a controlled rate, the rate being controlled primarily so as to maintain the desired temperature of the resultant reaction mixture. The reaction mixture should be stirred to ensure intimate mixing and to provide a substantially uniform temperature in the reaction mixture.

In a preferred embodiment of the process of the present invention cyanoacetylene is contacted with the amine in the presence of an inert solvent. Examples of suitable solvents are diethyl ether, tetrahydrofuran, dioxane, methanol, ethanol, dimethoxyethane ("glyme"), bis(2-methoxyethane) ether ("diglyme") and chlorinated solvents, e.g., methylene chloride. Preferably, the cyanoacetylene and the amine are each dissolved in the solvent prior to being brought into contact with each other. When the reaction is carried out in the presence of solvent it is preferred that one reactant be present in molar excess. For example, if the solution of cyanoacetylene in solvent is added to the solution of amine in solvent it is preferred that the amine be present in molar excess. The use of solvent is a factor in controlling the rate of reaction between the two reactants and a factor in controlling the temperature of the reaction mixture.

The reaction mixture is maintained at a temperature of not greater than the boiling point of both the amine and cyanoacetylene and moreover, below 40° C. if the amine has a boiling point in excess of 40° C. Furthermore if $R_1$ is alkyl or —$(CH_2)_n$—NH—CH=CH—CN the temperature is maintained at not greater than 30° C. The temperature may be controlled by, for example, cooling the reaction mixture and/or the reactants, and/or by controlling the rate at which the two reactants, cyanoacetylene and amine, are brought into contact. The temperature of the reaction mixture is preferably maintained as low as is practical to reduce the formation of decomposition products of the reactants or products.

In the process of the invention cyanoacetylene is contacted with the amine in the presence of an inert atmosphere. In particular, oxygen should be excluded from the reaction mixture to the extent that is practical. A suitable inert atmosphere is nitrogen.

The N-($R_1R_2$)-3-aminoacrylonitrile product of the reaction of cyanoacetylene and the amine is recovered from the reaction mixture at a temperature of less than 50° C. Techniques suitable for the recovery and purification of the N-($R_1R_2$)-3-aminoacrylonitrile are known. For example, volatile matter may be removed from the reaction mixture, under vacuum if desirable, while maintaining the reaction mixture at a temperature of less than 50° C. The N-($R_1R_2$)-3-aminoacrylonitrile may then be further separated from reactants, if necessary, and purified. The N-($R_1R_2$)-3-aminoacrylonitrile may be converted to a suitable salt especially the hydrochloride, separated and purified if necessary and reconverted to the N-($R_1R_2$)-3-aminoacrylonitrile. The product may be purified by other techniques, in particular, by contacting the product with silica, for example, by dissolving the product in a solvent, e.g., benzene/methanol, or by contacting with, for example, activated charcoal. If the product has a sufficiently high melting point recrystallization techniques may be used in the separation and/or purification of the product. The separation and purification of the product, N-($R_1R_2$)-3-aminoacrylonitrile, is carried out at temperatures of less than 50° C., and preferably less than 40° C., in order to reduce the decomposition of and/or other reactions of the product.

Step (a) of the process of the present invention may be carried out in the presence of a catalyst, e.g., cuprous chloride.

The present invention is illustrated by the following examples.

EXAMPLE I 0.50 g of cyanoacetylene in 3.5 of diethyl ether were added over a period of 30 minutes to a solution of 3.37 g of methylamine in 30 ml of diethyl ether. At atmosphere of nitrogen was maintained over the resultant reaction solution. The temperature of the reaction solution was maintained in the range $-12°$ to $-6°$ C. After 45 minutes the solvent and the reamining reactants were removed under vacuum. A yellow liquid of N-(methyl)-3-aminoacrylonitrile was obtained. The yield was 87.8% based on the amount of cyanoacetylene.

Analysis by nuclear magnetic resonance spectroscopy (N.M.R.) showed the presence of two isomers, the ratio of the cis isomer to the trans isomer being 93:7. The identity of the product was confirmed using infra red, laser raman and mass spectroscopy. Thermal Analysis showed that the product decomposed at 255° C.

EXAMPLE II 0.50 g of cyanoacetylene in 10 ml of diethyl ether were added over a period of 15 minutes to a solution of 6.83 g of ethylamine in 30 ml of diethyl ether. The temperature of the resultant reaction solution was 2° C. An atmosphere of nitrogen was maintained at 0° C. for 3 hours before the solvent and remaining reactants were removed under vacuum. A yellow liquid of N-ethyl-3-aminoacrylonitrile was obtained. The yield was 84.2% based on the amount of cyanoacetylene.

Analysis by N.M.R. spectroscopy showed the presence of two isomers, the ratio of the cis isomer to the trans isomer was 77:23. The product was characterized by micro-analysis and ultraviolet, infra red, laser raman and mass spectoscopy. Thermal analysis showed that the product decomposed at 260° C.

EXAMPLE III 0.5 g of cyanoacetylene in 5 ml of methanol were added over a period of 30 minutes to a solution of 18.4 g of diethylamine in 20 ml of methanol. The diethylamine solution contained a copper catalyst by adding 2.08 gm of hydroxylamine hydrochloride and then 21 mg of cuprous chloride to the diethylamine solution. The temperature of the resultant reaction solution was maintained below 8° C. and an atmosphere of nitrogen was maintained over the solution. After approximately 2 hours 30 ml of water were added and the resultant solution was extracted with diethyl ether. The diethyl ether solution was dehydrated, purified using charcoal and then the diethyl ether was removed under vacuum to give a yellow liquid of N,N-diethyl-3-aminoacrylonitrile in 85.2% yield, based on the amount of cyanoacetylene.

The N,N-diethyl-3-aminoacrylonitrile was characterized using micro-analysis and N.M.R., infra red, laser raman and mass spectroscopy. Thermal analysis showed that the product decomposed at 244° C.

EXAMPLE IV 0.50 g of cyanoacetylene were added over a period of 15 minutes to 11.1 g of butylamine (15 ml). The butylamine contained a copper catalyst prepared in a similar manner to that of Example III. The temperature of the resultant reaction solution was maintained below 38° C. and an atmosphere of nitrogen was maintained over the solution. After approximately 2 hours at 12°–16° C., 30 ml of water were added and the resultant solution was extracted with diethyl ether. The diethyl ether solution was dehydrated, purified with charcoal and then the diethyl ether was removed under vacuum to give a yellow liquid of N-butyl-3-aminoacrylonitrile in 72.4% yield.

Analysis by N.M.R. spectroscopy showed two isomers in the ratio of 80:20. The product was characterized by microanalysis and by infra red, laser raman and mass spectroscopy. Thermal analysis showed that the product decomposed at 254° C.

EXAMPLE V 0.62 g of cyanoacetylene in 3.5 ml of diethyl ether were added over a period of 15 minutes to a solution of 1.0 g of hexylamine in 30 ml of diethyether. The temperature of the resultant reaction solution was maintained below 28° C. and an atmosphere of nitrogen was maintained over the solution. After 2 hours the diethyl ether and unreacted monomers were removed under vacuum and a yellow liquid of N-hexyl-3-aminoacrylonitrile was obtained in 87% yield.

Analysis by N.M.R. spectroscopy showed the presence of cis and trans isomers in approximately a 1:1 ratio.

EXAMPLE VI 1.16 g of hexamethylenediamine were dissolved in 60 ml of methylene chloride and the solution was then filtered. 1.24 g of cyanoacetylene in 4 ml of diethyl ether were added over a period of 15 minutes. The temperature was maintained below 28° C. and an atmosphere of nitrogen was maintained over the reaction solution. After 2 hours the methylene chloride and unreacted cyanoacetylene were removed under vacuum. A green solid was obtained and on recrystallization, white crystals, m.p. 105° C. of N,N'bis(3-acrylonitrile)-hexamethylene diamine were obtained in 87% yield. The product was shown to be the cis isomer by N.M.R. spectroscopy.

EXAMPLE VII 0.5 g of liquid cyanoacetylene, cooled to 0° C., were slowly added over a period of 30 minutes to 1.02 g of liquid ethylamine which had been cooled to 0° C. A strongly exothermic reaction occurred and the temperature of the reaction mixture was maintained below 5° C. using an ice bath. An atmosphere of cyanoacetylene was completed, the reaction mixture was maintained as such for 30 minutes before any remaining reactants were removed under vacuum. a yellow liquid, N-ethyl-3-aminoacrylonitrile, was obtained. The yield was 64.4% based on the amount of cyanoacetylene.

The properties of the product obtained were identical to those of the product of Example II.

EXAMPLE VIII 1.23 g of cyanoacetylene in 10 ml of diethyl ether were added slowly to a solution of 1.86 g of aniline in 20 ml of diethyl ether. An atmosphere of nitrogen was maintained over the reaction mixture. The temperature of the reaction mixture was maintained in the range 18° to 21° C. Analysis showed that the reaction was 75% complete after 6 hours; the reaction was allowed to continue for a total of 24 hours by which time the reaction was 95.4% complete. The solvent and any remaining reactants were removed under vacuum. 2.73 g of a crystalline solid, a yield of 94.8%, were obtained.

The solid, N-phenyl-3-aminoacrylonitrile, was analyzed for C, H and N (calculated: C 74.98%, H 5.59%, N 19.43%, and found: C 74.83%, H 5.61%, N 19.40%) and the molecular structure was confirmed by infra red spectroscopy.

EXAMPLE IX 1.53 g of cyanoacetylene in 5 ml of diethyl ether were added over a period of 5 minutes to a solution of 2.16 g of p-toluidine in 10 ml of diethyl ether. An atmosphere of nitrogen was maintained over the reaction mixture. The temperature of the reaction mixture was maintained in the range 19° to 34° C. After a period of 3 hours the solvent and any remaining reactants were removed under vacuum. 3.12 g of product, a yield of 98.1%, were obtained.

The product, N-(p-methyl phenyl)-3-aminoacrylonitrile, was analyzed for C, H and N (calculated: C 75.44%, H 6.33%, N 17.60% and found: C 75.77%, H 6.45%, N 17.61%).

EXAMPLE X 1.94 g of cyanoacetylene were slowly added to a solution of 1.08 g of p-phenylene diamine (1,4 diamino benzene) in 30 ml of diethyl ether. An atmosphere of nitrogen was maintained over the reaction mixture. The temperature of the reaction mixture was maintained at ambient temperature (ca 20° C.). After 4.5 hours the solvent and volatile reactants were removed under vacuum. The product was purified by dissolving in acetone and reprecipitating by admixing the resultant solution with distilled water. The suspension, now essentially free of unreacted amine, was centrifuged and dried.

The product, N,N'-bis(3-acrylonitrile)-p-phenylene diamine, was analyzed for C, H and N (calculated: C 68.55%, H 4.79%, N 26.65% and found: C 68.27%, H 4.91%, N 26.41%) and the molecular structure was confirmed by infra red and mass spectroscopy.

We claim:

1. A process for the manufacture of N-(substituted)-3-aminoacrylonitriles of the formula N-($R_1R_2$)—CH=CH—CN where $R_1$ is alkyl, —($CH_2$)$_n$—NH—CH=CH—CN, phenyl or phenyl substituted with alkyl and/or —$NH_2$ groups, and $R_2$ is hydrogen or alkyl with the proviso that when $R_1$ is —($CH_2$)$_n$—NH—CH=CH—CN $R_2$ is hydrogen, n being 1 to 8, said process comprising the step of:
    (a) contacting cyanoacetylene with an amine selected from the group consisting of (i) $NHR_1R_2$, where $R_1$ is alkyl, phenyl or phenyl substituted with alkyl and/or —$NH_2$ groups and $R_2$ is as above, and (ii) $NH_2$—($CH_2$)$_n$—$NH_2$, where n is 1 to 8, in the presence of an inert atmosphere and at a temperature below the boiling point of cyanoacetylene and of said amine, said temperature being not greater than 40° C., with the proviso that when $R_1$ is alkyl or —($CH_2$)$_n$—NH—CH=CH—CN the temperature is not greater than 30° C., and
    (b) recovering the N-($R_1R_2$)-3-aminoacrylonitrile so obtained at a temperature of not greater than 50° C.

2. The process of claim 1 in which the cyanoacetylene is contacted with the amine in the presence of an inert solvent.

3. The process of claim 2 in which the substituent $R_2$ is hydrogen.

4. The process of claim 3 in which the substituent $R_1$ is alkyl of 1 to 6 carbon atoms and the temperature in step (a) is maintained at not greater than 30° C.

5. The process of claim 3 in which the substituent $R_1$ is —($CH_2$)$_n$—NH—CH=CH—CN and the amine is $NH_2$—($CH_2$)$_n$—$NH_2$, n being 1 to 8.

6. The process of claim 5 in which n is 6.

7. The process of claim 23 in which the substituent $R_1$ is phenyl.

8. The process of claim 3 in which the substituent $R_1$ is phenyl substituted with alkyl and/or —$NH_2$.

* * * * *